(12) United States Patent
Wagner et al.

(10) Patent No.: US 10,176,375 B2
(45) Date of Patent: Jan. 8, 2019

(54) HIGH SPEED PUPIL DETECTION SYSTEM AND METHOD

(71) Applicant: RAYTHEON CANADA LIMITED, Ottawa (CA)

(72) Inventors: Kevin B. Wagner, Wyevale (CA); Ryan W. Nobes, New Lowell (CA)

(73) Assignee: Raytheon Canada Limited, Ottawa (CA)

( * ) Notice: Subject to any disclaimer, the term of this patent is extended or adjusted under 35 U.S.C. 154(b) by 51 days.

(21) Appl. No.: 15/472,753

(22) Filed: Mar. 29, 2017

(65) Prior Publication Data

US 2018/0285620 A1     Oct. 4, 2018

(51) Int. Cl.
*G06K 9/00*     (2006.01)
*G06T 7/73*     (2017.01)

(52) U.S. Cl.
CPC ....... *G06K 9/0061* (2013.01); *G06K 9/00604* (2013.01); *G06T 7/74* (2017.01); *G06T 2207/10016* (2013.01); *G06T 2207/10048* (2013.01); *G06T 2207/30201* (2013.01)

(58) Field of Classification Search
CPC .... G06K 9/0061; G06K 9/00604; G06T 7/74; G06T 2207/10016; G06T 2207/10048; G06T 2207/30201
USPC .......................................................... 348/78
See application file for complete search history.

(56) References Cited

U.S. PATENT DOCUMENTS

| | | | |
|---|---|---|---|
| 4,973,149 A | * | 11/1990 | Hutchinson ............ A61B 3/113 351/210 |
| 6,005,710 A | | 12/1999 | Pensel et al. |
| 6,157,352 A | | 12/2000 | Kollin et al. |
| 6,204,829 B1 | | 3/2001 | Tidwell |
| 6,394,602 B1 | | 5/2002 | Morrison et al. |
| 6,433,760 B1 | | 8/2002 | Vaissie et al. |
| 6,473,246 B1 | | 10/2002 | Chao |
| 6,634,749 B1 | | 10/2003 | Morrison et al. |

(Continued)

FOREIGN PATENT DOCUMENTS

| | | |
|---|---|---|
| WO | 2000026713 A1 | 5/2000 |
| WO | 2013103443 A1 | 7/2013 |

OTHER PUBLICATIONS

International Search Report and Written Opinion for application No. PCT/CA2018/000016 dated May 10, 2018.

(Continued)

*Primary Examiner* — Jamie J Atala
*Assistant Examiner* — James T Boylan
(74) *Attorney, Agent, or Firm* — Lando & Anastasi, LLP

(57) ABSTRACT

Aspects are generally directed to a high speed pupil detection system and method. In one example, the method includes receiving optical radiation reflected from an eye at one or more pixels of an optical sensor, reading-out a value of each of the pixels in a plurality of lines to progressively generate an image frame of a video image stream, the value of each of the pixels being based on a flux of the received optical radiation, identifying a first chord within a first line of the plurality of lines, identifying a second chord within a second line of the plurality of lines, the first chord and second chord being separated by a subset of the plurality of lines, and determining a location of a center of a pupil of the eye based on a two chord crossing of the pupil with the first chord and the second chord.

15 Claims, 9 Drawing Sheets

(56) References Cited

U.S. PATENT DOCUMENTS

| | | |
|---|---|---|
| 8,360,583 B2 | 1/2013 | Watanabe |
| 9,557,553 B2 | 1/2017 | Szapiel |
| 2001/0011968 A1 | 8/2001 | Tidwell |
| 2002/0167462 A1 | 11/2002 | Lewis et al. |
| 2003/0086057 A1* | 5/2003 | Cleveland .............. A61B 3/113 351/204 |
| 2010/0302499 A1 | 12/2010 | Watanabe |
| 2013/0010097 A1 | 1/2013 | Durnell et al. |
| 2013/0077024 A1 | 3/2013 | Shikii et al. |
| 2013/0170022 A1 | 7/2013 | Caldeira et al. |
| 2015/0103155 A1* | 4/2015 | Szapiel .................. G02B 23/14 348/78 |
| 2016/0223819 A1* | 8/2016 | Liu .................... G02B 27/0172 |
| 2017/0134643 A1* | 5/2017 | Kim ........................ G06T 7/246 |

OTHER PUBLICATIONS

Curatu et al., "Projection-based head-mounted display with eye-tracking capabilities", Proceeding of SPIE, vol. 5875, Novel Optical Systems Design and Optimization VIII, (2005).

* cited by examiner

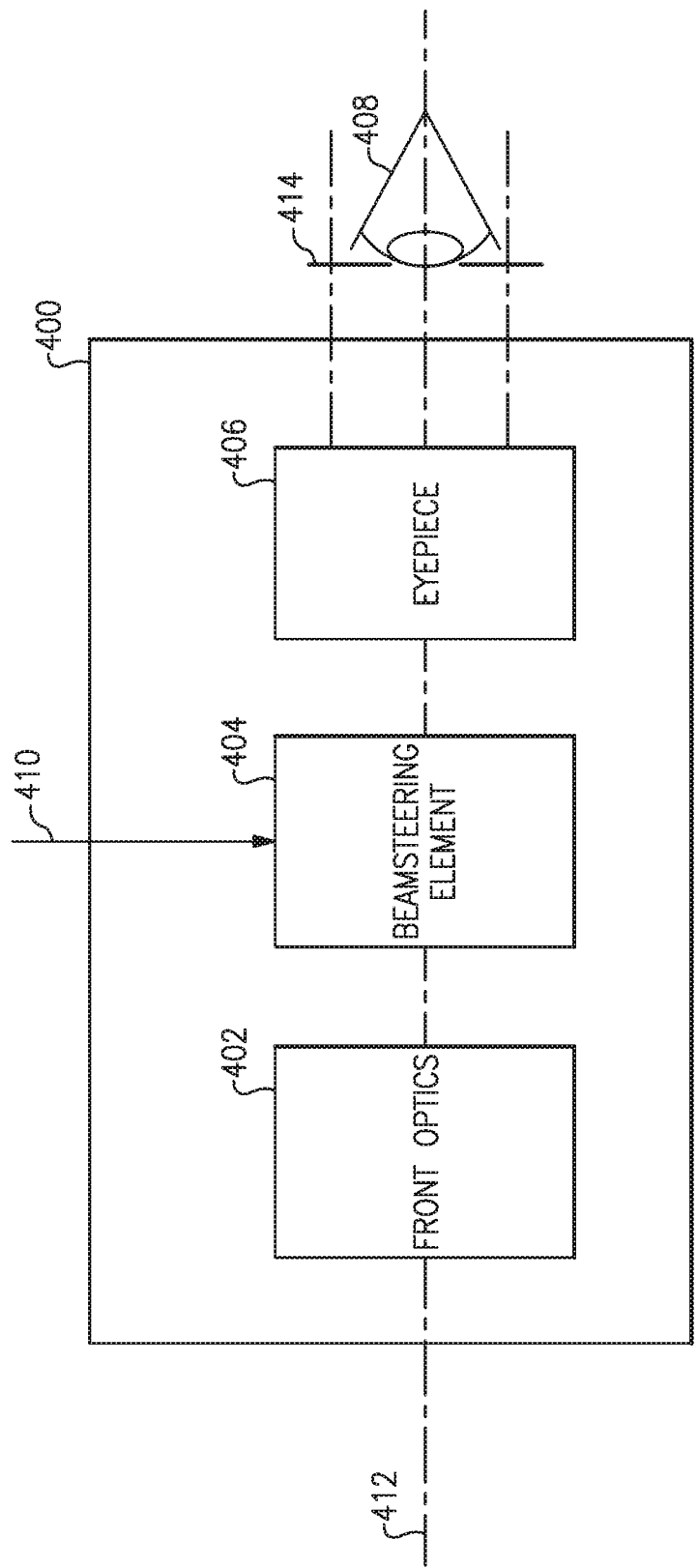

HIGH SPEED PUPIL DETECTION SYSTEM AND METHOD

BACKGROUND

Magnified telescopic sights, such as rifle scopes and spotting scopes, frequently suffer from a very small exit pupil size. When the exit pupil diameter of the device is approximately the same size or smaller than the diameter of the pupil of the operator's eye, it is challenging to keep the eye within the effective eyebox of the device. Moving the eye out of the eyebox may result in severe vignetting or total loss of the observed scene.

For example, if the diameter of the exit pupil of a telescope is about 2 millimeters (mm) or less, the operator must try to keep his/her head extremely stable, even if the device is equipped with a tripod, in order to keep the eye within the eyebox. Very small, sub-millimeter movements of the operator's head can have significant impact. Therefore, even people who are trained to work with instruments having tight eyeboxes may not be able to keep their heads sufficiently stable, particularly under such circumstances as intensive physical effort (for example, after a fast run), stress, or exhaustion. In addition, it may take several seconds to achieve a proper match between the operator's eye and the eyebox of the device.

Accordingly, various systems have been designed to automatically detect a misalignment between an operator's eye and an eyebox of a telescopic device. These systems typically use imaged eye movements to control other functions of the telescopic device to compensate for the misalignment. For instance, some systems implement feature extraction techniques using image analysis, such as a Hough transform, over the duration of multiple frames of a video output stream.

SUMMARY OF THE INVENTION

Aspects and embodiments are generally directed to a high speed pupil detection system and method for determining the location of a center of a pupil from a single image frame of a continuous video image stream. As discussed in further detail below, examples of the system receive reflections of optical radiation from an eye at one or more pixels of an optical sensor. Responsive to receiving the reflected optical radiation, a value of each of the one or more pixels are read-out in a plurality of lines to progressively generate an image frame. While the pixels are being scanned (i.e., read-out), the system is configured to analyze the scanned lines of the image frame to identify a first chord and a second chord. Once identified, the system determines a location of the center of the pupil based on a two chord crossing of the pupil with the first chord and the second chord. In this manner, aspects of the system and method described herein reduce the computational complexity, and improve the executional efficiency, when compared to typical pupil detection techniques. Moreover, pupil positioning measurements performed during a single image frame of a continuous video stream substantially increases the speed by which corrective measures may be performed by an associated optical device.

As further described below, examples of optical devices in which examples of the system and method may be used may include, but are not limited to, telescopic sights (such as rifle scopes, spotting scopes, etc.), microscopes, endoscopes, other optical imaging devices which have an optical assembly that produces a remotely located real exit pupil, or other optical imaging devices which perform operations based on a pupil location or gaze direction of a human operator (e.g., an aircraft pilot's helmet video display). Further advantages and benefits of the disclosed high speed pupil detection system and method are described below with reference to the drawings.

According to an aspect, provided is a method of pupil detection. In one example, the method comprises receiving optical radiation reflected from an eye at one or more pixels of an optical sensor, reading-out a value of each of the one or more pixels in a plurality of lines to progressively generate a first image frame of a video image stream, the value of each of the one or more pixel being based on a flux of the received optical radiation, identifying a first chord within a first line of the plurality of lines, identifying a second chord within a second line of the plurality of lines, the second chord being separated from the first chord by a subset of the plurality of lines, and determining a first location of a center of a pupil of the eye in a first dimension and in a second dimension orthogonal to the first dimension based on a two chord crossing of the pupil with the first chord and the second chord.

In various examples, identifying the first chord includes identifying the first chord while reading-out the value of each of the one or more pixels, and identifying the second chord includes identifying the second chord while reading-out the value of each of the one or more pixels. According to certain examples, the method further comprises identifying a third chord within a third line of the plurality of lines, while reading-out the value of each of the one or more pixels, identifying a fourth chord within a fourth line of the plurality of lines, while reading-out the value of each of the one or more pixels, and determining a second location of the center of the pupil in the first dimension and in the second dimension based on a two chord crossing of the pupil with the third chord and the fourth chord. In a further example, the method further comprises averaging the first location and the second location.

According to various examples, identifying the first chord includes detecting a first start trigger and detecting a first stop trigger, and identifying the second chord includes detecting a second start trigger and detecting a second stop trigger. In certain examples, each of the first start trigger and the first stop trigger include a transition in a brightness level along the first line, and each of the second start trigger and the second stop trigger include a transition in a brightness level along the second line. In at least one example, the transition in the brightness level along the first line is an intersection point between the first line and a perimeter of the pupil, and the transition in the brightness level along the second line is an intersection point between the second line and the perimeter of the pupil.

In certain examples, determining the location of the center of the pupil in the first dimension includes determining the location of the center of the pupil in the first dimension according to:

$$C_X = \frac{Stop_1 - Start_1}{2} + Start_1$$

where $C_X$ is the location of the center of the pupil in the first dimension, $Stop_1$ is a coordinate of the first stop trigger, and $Start_1$ is a coordinate of the first start trigger.

According to certain examples, determining the location of the center of the pupil in the second dimension includes determining an intermediary center according to:

$$\text{Center} = \frac{\left(\frac{Stop_2 - Start_2}{2}\right)^2 - \left(\frac{Stop_1 - Start_1}{2}\right)^2 - ChordSpacing^2}{2 * ChordSpacing}$$

where Center is the intermediary center, $Stop_2$ is a coordinate of the second stop trigger, $Start_2$ is a coordinate of the second start trigger, and ChordSpacing is the subset of the plurality of lines.

In various examples, determining the location of the center of the pupil of the eye in the second dimension includes determining the location of the center of the pupil in the second dimension according to:

$C_Y$=LineNumber+ChordSpacing+Center where $C_Y$ is the location of the center of the eye in the second dimension and LineNumber is a line iteration number of the second line of the plurality of lines.

According to certain examples, the method further comprises projecting optical radiation onto the eye with an infrared illuminator, the optical radiation including infrared radiation. In various examples, the method further comprises adjusting a beamsteering element of an optical assembly to position a real exit pupil to reduce an offset between the first location of the center of the pupil and the real exit pupil.

According to an aspect, provided is a pupil detection system. In one example, the pupil detection system comprises an optical illuminator configured to project optical radiation onto an eye, an optical sensor positioned to receive reflections of the optical radiation from the eye and progressively generate in a plurality of lines a first image frame of a video image stream, and a digital image processor unit coupled to at least the optical sensor and configured to: identify a first chord within a first line of the plurality of lines, identify a second chord within a second line of the plurality of lines, the second chord being separated from the first chord by a subset of the plurality of lines, and determine a first location of a center of a pupil of the eye in a first dimension and in a second dimension orthogonal to the first dimension based on a two chord crossing of the pupil with the first chord and the second chord.

In various examples, the optical illuminator is an infrared illuminator positioned to project infrared radiation onto the eye. In certain examples, the pupil detection system further comprises an optical assembly including at least an eyepiece configured to produce a real exit pupil, and the digital image processor is further configured adjust the optical assembly to position the real exit pupil to reduce an offset between the first location of the center of the pupil and the real exit pupil.

According to various examples, the digital image processor is further configured to identify the first chord while the optical sensor progressively generates the first image frame, and identify the second chord while the optical sensor progressively generates the first image frame. In certain examples, the digital image processor is further configured to: identify a third chord within a third line of the plurality of lines, while the optical sensor progressively generates the first image frame, identify a fourth chord within a fourth line of the plurality of lines, while the optical sensor progressively generates the first image frame, determine a second location of the center of the pupil in the first dimension and in the second dimension based on a two chord crossing of the pupil with the third chord and the fourth chord, and average the first location and the second location.

In certain examples, in identifying the first chord the digital image processor unit is configured to detect a first start trigger and detect a first stop trigger, and in identifying the second chord the digital image processor unit is configured to detect a second start trigger and detect a second stop trigger. In various examples, each of the first start trigger and the first stop trigger include a transition in a brightness level along the first line, and each of the second start trigger and the second stop trigger include a transition in a brightness level along the second line.

Still other aspects, embodiments, and advantages of these exemplary aspects and embodiments are discussed in detail below. Embodiments disclosed herein may be combined with other embodiments in any manner consistent with at least one of the principles disclosed herein, and references to "an embodiment," "some embodiments," "an alternate embodiment," "various embodiments," "one embodiment" or the like are not necessarily mutually exclusive and are intended to indicate that a particular feature, structure, or characteristic described may be included in at least one embodiment. The appearances of such terms herein are not necessarily all referring to the same embodiment. Various aspects and embodiments described herein may include means for performing any of the described methods or functions

BRIEF DESCRIPTION OF THE DRAWINGS

Various aspects of at least one embodiment are discussed below with reference to the accompanying figures, which are not intended to be drawn to scale. The figures are included to provide illustration and a further understanding of the various aspects and embodiments, and are incorporated in and constitute a part of this specification, but are not intended as a definition of the limits of the invention. In the figures, each identical or nearly identical component that is illustrated in various figures is represented by a like numeral. For purposes of clarity, not every component may be labeled in every figure. In the figures:

FIG. 4A is a block diagram of an optical assembly according to one or more examples discussed herein;

DETAILED DESCRIPTION

Figure 1:
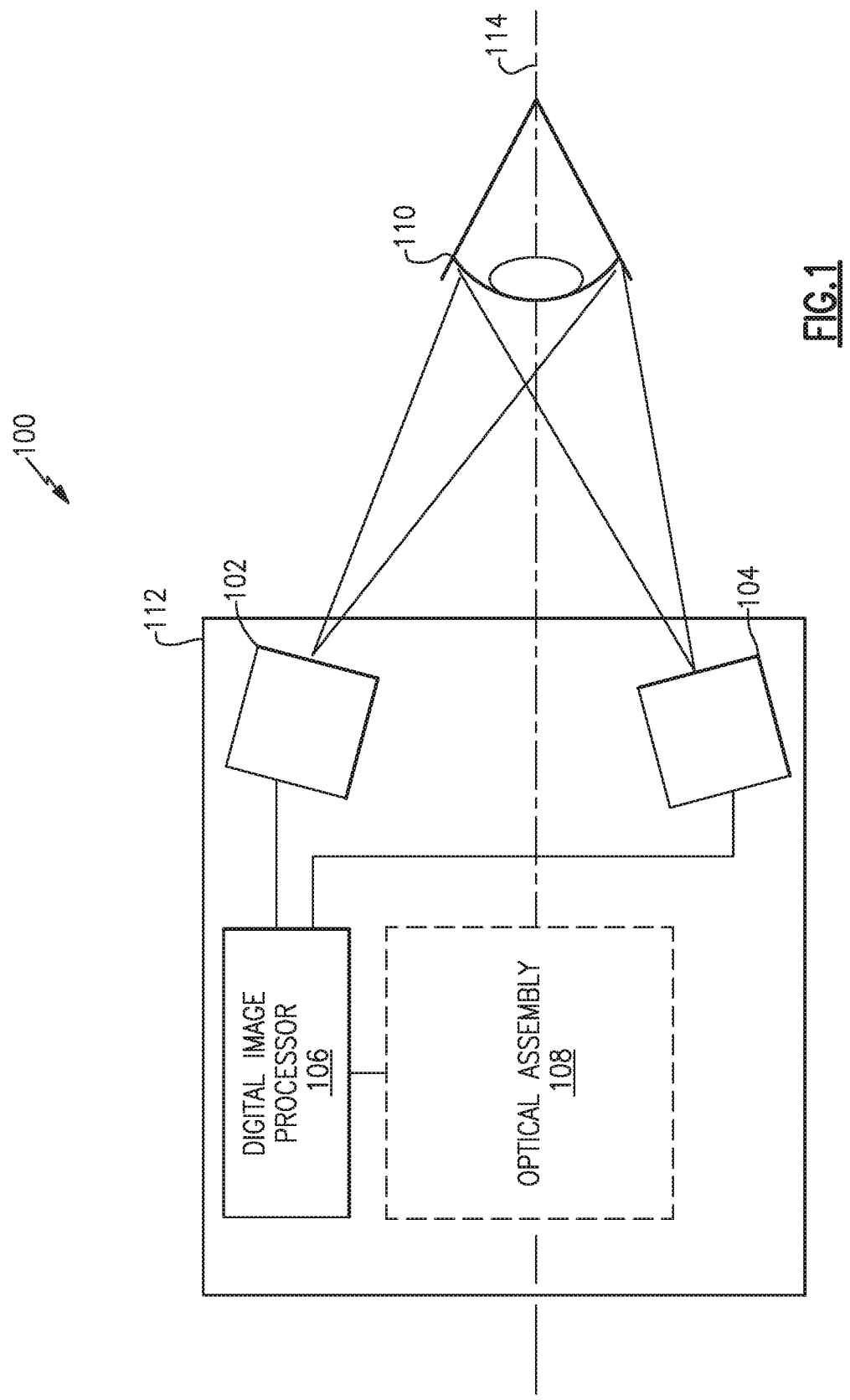
FIG. 1 is a block diagram of a high speed pupil detection system according to one or more examples discussed herein.

Aspects and embodiments are generally directed to a high speed pupil detection system and method. Examples of the system use lines of video information from a progressive scan of an eye to determine the location of a pupil center. In particular, the system is configured to identify a first chord and a second chord, and determine the location of the center of the pupil based on a two-chord crossing of the pupil with the first chord and the second chord. As further described below, examples of optical devices in which the system and method may be used may include, but are not limited to, telescopic sights, microscopes, endoscopes, other optical imaging devices which have an optical assembly that produces a remotely located real exit pupil, and other optical imaging devices which perform operations based on a pupil location or gaze direction of a human operator.

As discussed above, various approaches exist for eye-movement detection and/or gaze detection. These approaches typically apply a Hough transform to a series of full frame video images to extract features of an eye. Based on the similarities and dissimilarities in features across multiple frames, a position of the eye may be ascertained. These approaches can be computationally intensive and often require high powered processing components to execute the described techniques. Moreover, the acquisition delay between each video image frame makes high speed detection challenging.

Accordingly, various aspects and embodiments of the pupil detection system and method described herein reduce the computational complexity of current pupil tracking techniques. Moreover, pupil positioning measurements performed during a single image frame of a continuous video image stream, as described herein, substantially increases the speed by which corrective measures may be performed by an associated optical device. Accordingly, various aspects and embodiments of the pupil detection system and method described herein provide high speed and real time pupil detection functionality that is not currently offered by existing optical devices and imaging techniques.

It is to be appreciated that embodiments of the systems and apparatuses discussed herein are not limited in application to the details of construction and the arrangement of components set forth in the following description or illustrated in the accompanying drawings. The systems and apparatuses are capable of implementation in other embodiments and of being practiced or of being carried out in various ways. Examples of specific implementations are provided herein for illustrative purposes only and are not intended to be limiting. Also, the phraseology and terminology used herein is for the purpose of description and should not be regarded as limiting. The use herein of "including," "comprising," "having," "containing," "involving," and variations thereof is meant to encompass the items listed thereafter and equivalents thereof as well as additional items. References to "or" may be construed as inclusive so that any terms described using "or" may indicate any of a single, more than one, and all of the described terms. Any references to front and back, left and right, top and bottom, upper and lower, and vertical and horizontal are intended for convenience of description, not to limit the present systems and methods or their components to any one positional or spatial orientation.

Referring to FIG. 1, there is illustrated a block diagram of one example of a high speed pupil detection system 100. As discussed above, the system 100 may be implemented in any suitable type of optical imaging device or telescope. The illustrated system 100 includes an optical illuminator 102, an optical sensor 104, a digital image processor unit 106, and, optionally, an optical assembly 108. The optical assembly 108 may include a plurality of optical elements positioned along an optical path 114 and which together direct and focus received light onto an operator's eye 110. For instance, the optical assembly 108 may include front optics and an eyepiece which work together to focus light received from a scene and/or target on the operator's eye 110 to permit the operator to view a scene and/or target. Certain examples of the optical assembly 108 are further discussed below with reference to FIG. 4A and FIG. 4B. Components of the high speed pupil detection system 100 illustrated in FIG. 1 may be enclosed within a housing 112 which protects the components from external forces and environmental influences, such as dust, moisture, and the like.

In various examples, pupil detection and location operations are accomplished using the optical illuminator 102, the optical sensor 104, and the digital image processor unit 106. The optical illuminator 102 is controlled to project optical radiation over an eye, which may be the eye 110 of the operator of the system 100, for example. For instance, the optical illuminator 102 may include a flash illuminator that illuminates an entire surface eye 110 from left to right and from top to bottom (relative to the eye 110). However, in certain other examples the optical illuminator 102 may include a progressive scan illuminator that progressively scans the eye 110 in synchronization with the optical sensor 104. In the illustrated example, the optical illuminator 102 is an infrared illuminator positioned to project infrared radiation over the eye 110 in a predetermined direction and over a field of view thereof in a continuous manner.

The optical sensor 104 is positioned to receive reflections of the optical radiation from the eye 110 and generate a first image frame based on the received reflections. In one example, the optical illuminator 102 and optical sensor 104 are synchronized to generate a continuous video stream of consecutive image frames. The optical sensor 104 may include any suitable image pickup device, such as a charge coupled device (CCD) or complementary metal-oxide semi-conductor (CMOS) sensor. The optical sensor 104 includes a plurality of individual detector elements, which may be referred to as pixels. The plurality of pixels may be arranged in a series of rows (e.g., in a horizontal direction) and columns (e.g., in a vertical direction), and may each be positioned to receive the optical radiation reflected from the eye 110. Each pixel of the plurality is configured to collect and integrate photons of the received optical radiation and provide a read-out value representative of the accumulated flux of the incident optical radiation. In one example, the system 100 may include a read-out integrated circuit (ROIC) (not shown in FIG. 1) which communicates read-out values to the digital image processor unit 106.

Figure 2:
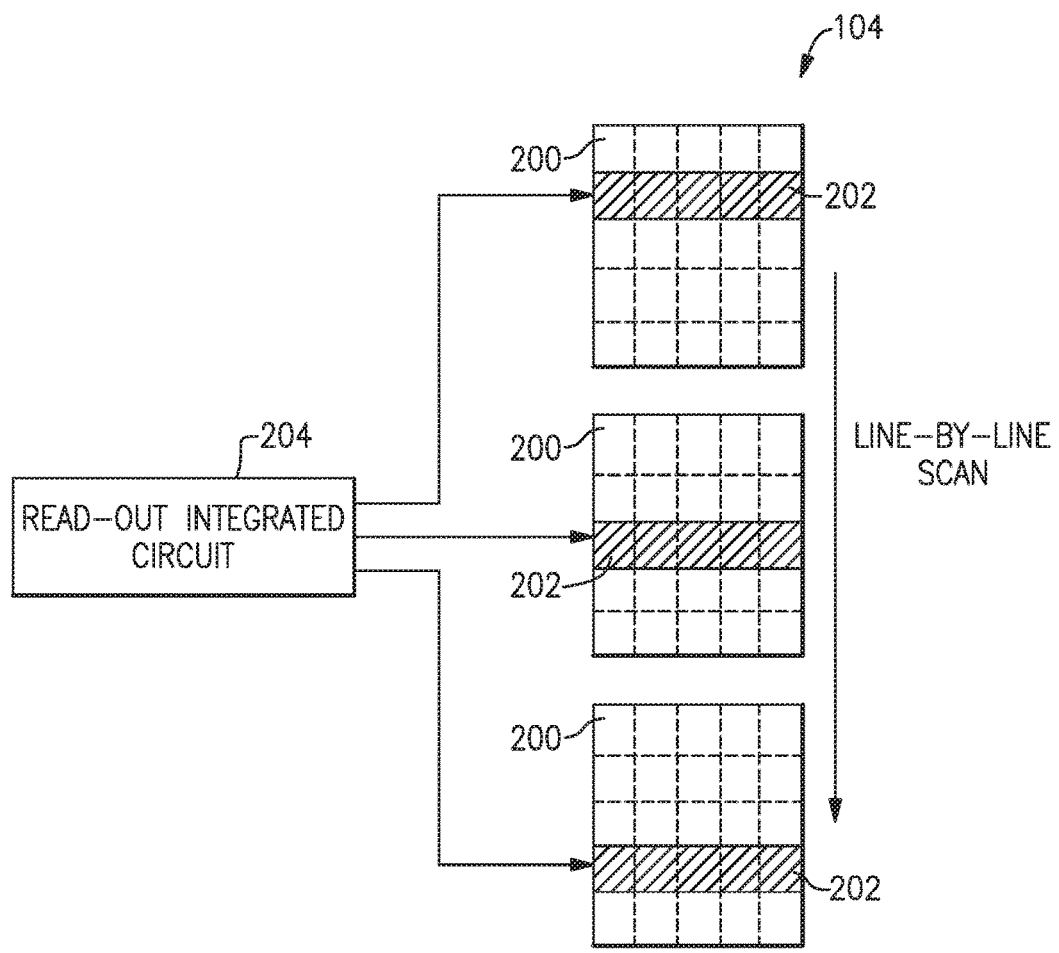
FIG. 2 is a diagram showing a line-by-line progressive scan of the pixels of an optical sensor, according to one or more examples discussed herein.

In various examples, the read-out values of the pixels within the optical sensor 104 are progressively scanned (i.e., read-out) line by line to build up a full image frame of the eye. Referring to FIG. 2, illustrated is a diagram showing a line-by-line progressive scan of the pixels 200 of the optical sensor 104 illustrated in FIG. 1. In one example, the read-out values of the pixels 200 are scanned (e.g., by the ROIC 204) in a sequential, line-by-line manner (indicated by scanned lines 202). FIG. 2 illustrates the optical sensor 104 as read-out from top to bottom (relative to the optical sensor 104). Although the term "line" may generally be used to refer to a set of pixels 200 in a horizontal direction, it may equally refer to a set of pixels 200 in the vertical direction. Accordingly, in various other examples pixels 200 of the optical sensor 104 may be read-out from bottom to top, from left to right, and/or from right to left, in a plurality of lines relative to the optical sensor 104. While FIG. 2 illustrates the ROIC 204 separated from the optical sensor 104, in various other examples the ROIC 204 may be an integrated component within the optical sensor 104 or within another component of the system 100, such as the digital image processor unit 106.

Accordingly, in certain examples, the optical sensor 104 may provide read-out values for each line of scanned image data. As discussed herein, each line of read-out values is referred to as line image information or line image data, and may include image data from each pixel within a row or column of the optical sensor 104. It is appreciated that the optical sensor 104 illustrated in FIG. 2 shows a simplified illustration of an optical sensor for the convenience of explanation. In various examples, the optical sensor 104 may include any suitable number of pixels 200 arranged any suitable pattern. For instance, the optical sensor 104 may have a resolution of 640×480, 700×480, or 768×576, to name a few examples.

Referring to FIG. 1, the digital image processor unit 106 is coupled and in electrical communication with the optical illuminator 102 and the optical sensor 104. The digital image processor unit 106 may send and receive one or more digital or analog signals with the optical illuminator 102 and the optical sensor 104. For instance, the digital image processor unit 106 may receive one or more read-out signals (e.g., line image data) from the optical sensor 104 as the optical sensor 104 is scanned. That is, in one example the optical sensor 104 may communicate line image data to the digital image processor unit 106 in a line-by-line manner as the read-out values are scanned from the optical sensor 104. Upon receiving the line image data, the digital image processor unit 106 may buffer, filter, and/or normalize the line image data prior to performing one or more operations to determine a location of a center of the pupil of the eye 110. While in one example the digital image processor unit 106 buffers, filters, and normalizes the line image data, in certain other examples the digital image processor unit 106 may perform other operations to format the received line image data.

For instance, the digital image processor unit 106 may average the read-out values for a predetermined sub-set of pixels along each scanned line across a length of the scanned line (e.g., a sliding average). The digital image processor unit 206 may then normalize the read-out values of the sub-sets of averaged pixels by subtracting the lowest averaged read-out value from the remaining averaged read-out values of the sub-sets of pixels. The digital image processor may then scale the scanned line to a maximum value by dividing a maximum value (e.g., a maximum read-out value of a pixel) by a maximum averaged read-out value of the scanned line. The resulting value, may be applied (e.g., multiplied) to each pixel read-out value within the scanned line prior to normalize the scanned line. Other processes executed by the digital image processor 106 to buffer, filter, and/or normalize the line image data may be tailored to the particular implementation of the high speed pupil detection system 100, and in particular, the specifications of the optical sensor 104 and/or the optical illuminator 102.

As the line image data is scanned (i.e., read-out), the digital image processor unit 106 analyzes each scanned line of the scanned plurality to identify a first chord and a second chord. As the line image data is received and analyzed, the digital image processor unit 106 may also assign a line iteration number to each line and increment the line iteration number as each subsequent line is scanned. In at least one example, a chord is a portion of a scanned line which extends between a start trigger and a stop trigger. Accordingly, the digital image processor unit 106 may analyze the line image data of each scanned line to identify a chord by searching for a start trigger and a stop trigger. It is appreciated that in many instances each line within the plurality of scanned lines of a single image frame may not possess a chord, and, accordingly, the digital image processor unit 106 may analyze many lines before a first chord and a second chord are identified.

Figure 3A:
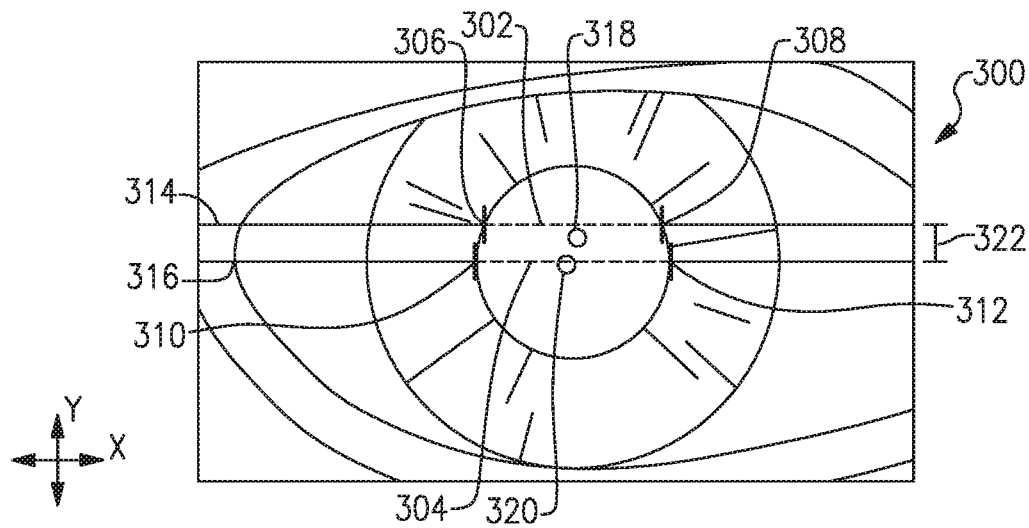
FIG. 3A is an image frame detected by the high speed pupil detection system of FIG. 1, according to one or more examples discussed herein.

Referring to FIG. 3A, illustrated is one example of a single image frame 300 of a continuous video image stream of the eye 110 shown in FIG. 1. That is, the shown image frame 300 is constructed from a plurality of scanned lines of the optical sensor 104. Within the image frame 300, a first chord 302 and a second chord 304 extend in a first dimension (e.g., horizontal direction, x) relative to the eye. Specifically, the first chord 302 extends across the pupil between a first start trigger 306 and a first stop trigger 308, and the second chord 304 extends across the pupil between a second start trigger 310 and a second stop trigger 312. The first chord 302 and the second chord 304 are separated in a second dimension (e.g., vertical dimension, y) by a subset of the plurality of lines (indicated by space 322).

In the illustrated example, the first chord 302 forms a portion of a first scanned line 314 and the second chord 304 forms a portion of a second scanned line 316. While illustrated in FIG. 3A as being scanned in a horizontal direction relative to the eye, in various other examples each of the first chord 302 and the second chord 304 may be identified as a portion of a corresponding line scanned in the vertical direction. For purpose of explanation only, the first line 314 has a line iteration number of 270 and the second line 316 has a line iteration number of 285.

The digital image processor unit 106 may identify the first chord 302 and the second chord 304 by searching for, and detecting, the corresponding start triggers and the corresponding stop triggers (i.e., start triggers 306, 310 and stop triggers 308, 312) of the first chord 302 and the second chord 304. The start trigger indicates the beginning of the corresponding chord and the stop trigger indicates the end of the corresponding chord. As also illustrated in FIG. 3A, each trigger 306, 308, 310, 312 is located at an intersection of the corresponding line 314, 316 and a perimeter of the pupil, within the image frame 300. That is, each of the first line 314 and second line 316 crosses the perimeter of the pupil for a first time at the corresponding start trigger 306, 310 and crosses the perimeter of the pupil for a second time at the corresponding stop trigger 308, 312. In at least one example, the digital image processor unit 106 is configured to detect a start trigger and/or a stop trigger based on a transition in a brightness level along a line of line image data.

As shown in FIG. 3A, the pupil often appears in black (or another dark hue) within the video image frame 300 as a result of diffusive reflections within the eye or light absorption by eye tissues during illumination by the optical illuminator 102. Accordingly, the digital image processor unit 106 may analyze a brightness level along each line of line image data and track brightness level transitions to identify a start or stop trigger. For instance, a transition from a high brightness level to a low brightness level (e.g., transition from the iris to the pupil) may indicate a start trigger, and a transition from a low brightness level to a high brightness level (e.g., transition from the pupil to the iris) may indicate a stop trigger. In at least one example, the digital image processor unit 106 may calculate the difference in brightness levels between two adjacent pixels (or multiple pixels) within a line of line image data and compare the difference to a threshold. If the threshold is exceeded, the digital image processor unit 106 may label the corresponding location (e.g., start or stop trigger coordinates) within the image frame as a start or stop trigger.

In at least one example, the number of lines within subset of the plurality of lines between the first line 314 and the second line 316 may be predetermined. Once the first chord 302 is identified, the digital image processor unit 106 may delay trigger detection operations for the second chord 304 until the specified number of lines has been scanned. In an example where the system 100 has a resolution of 640×480 at a frame rate of 30 FPS, the subset of the plurality of lines between the line 314 and the line 316 may be 15 lines, or any other suitable number. Accordingly, upon identifying the first chord 302 in line iteration number 270, the digital image processor unit 106 may delay trigger detection operations until the line iteration number 285 is reached.

In another example, the number of lines between the first line 314 and the second line 316 may be automatically and/or dynamically adjusted by the digital image processor unit 106. For instance, the digital image processor unit 106 may adjust the requisite spacing between the first chord 302 and the second chord 304 based on the quality of the image frame 300, the desired speed of the system 100, or a desired accuracy of the system 100.

Based on the first chord 302 and the second chord 304, the digital image processor unit 106 may determine a location of a center of the pupil in the first dimension and the second dimension by using a two-chord crossing of the first chord 302 and the second chord 304 with the pupil. For instance, in at least one example, the digital image processor unit 106 may execute a series of instructions which implement a two-chord crossing algorithm based on the first chord 302 and the second chord 304. Examples of steps and acts which may be performed within such an algorithm as discussed below with reference to FIG. 3A and FIG. 3B, as well as the example process flows illustrated in FIG. 6 and FIG. 7A-7B.

In at least one example, the digital image processor unit 106 determines the location of the center of the pupil by determining a location of the center of the pupil in the first dimension, determining an intermediary center, and determining a location of the center of the pupil in the second dimension. In FIG. 3A, a determined location of the center of the pupil based on the first and second chords 302, 304 is illustrated by center indicator 318.

In one example, the digital image processor unit 106 may determine the location of the center in the first dimension according to:

$$C_X = \frac{Stop_1 - Start_1}{2} + Start_1$$

where, $C_X$ is the location of the center of the pupil in the first dimension, $Stop_1$ is a coordinate of the first stop trigger 308, and $Start_1$ is a coordinate of the first start trigger 306. Each coordinate may correspond to a pixel position within the optical sensor 104. For instance, each coordinate may be a row or column number of a pixel within the optical sensor 104.

In one example, the digital image processor unit 106 may determine the intermediary center according to:

$$Center = \frac{\left(\frac{Stop_2 - Start_2}{2}\right)^2 - \left(\frac{Stop_1 - Start_1}{2}\right)^2 - ChordSpacing^2}{2 * ChordSpacing}$$

where, Center is the intermediary center, $Stop_2$ is a coordinate of the second stop trigger 312, $Start_2$ is a coordinate of the second start trigger 310, and ChordSpacing is the subset of the plurality of lines. The intermediary center is a computational value that simplifies the processes for determining the location of the center of the eye in the second dimension.

Once the intermediary center is determined, the digital image processor unit 106 may determine the location of the center of the pupil in the second dimension. For instance, the digital image processor unit 106 may determine this location according to:

$$C_Y = LineNumber + ChordSpacing + Center$$

where, $C_Y$ is the location of the center of the eye in the second dimension and LineNumber is a line iteration number of the second line 316 of the plurality of scanned lines.

While in one instance, the digital image processor unit 106 is configured to determine the location of the center of the pupil in the first dimension and the second dimension based on a single two-chord crossing, in various examples, as a result of the speed and executional efficiency of the system 100, the digital image processor unit 106 may perform multiple iterations of the described pupil location operations during a single image frame of a continuous video stream. That is, the digital image processor unit 106 may perform numerous on-the-fly measurements in real time during the progressive image read-out of a single image frame. Each on-the-fly measurement may be averaged over the course of the single image frame to determine an average pupil center location. A determined location of the center of the pupil based on a plurality of averaged two-chord crossings is illustrated by center indicator 320 in FIG. 3A.

Figure 3B:
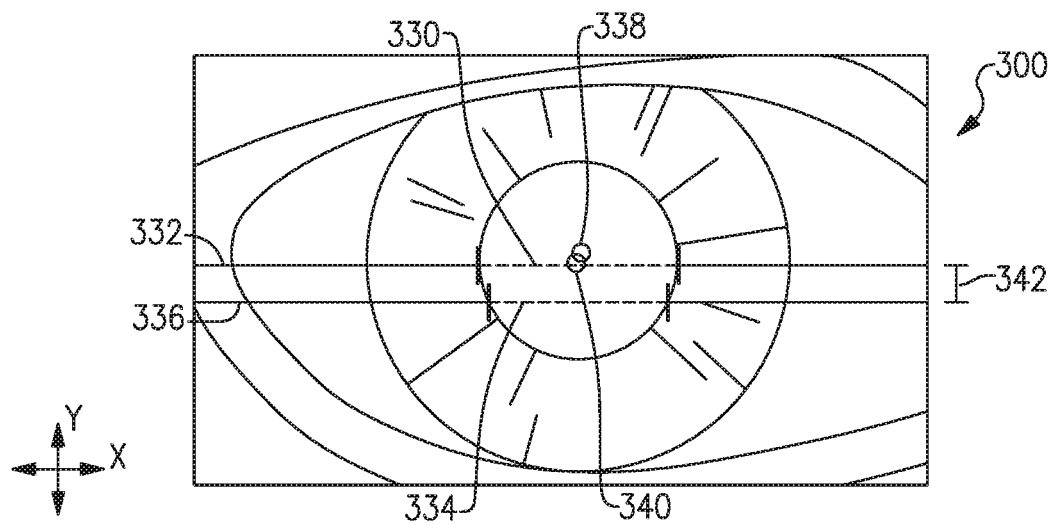
FIG. 3B is another example of the image frame of FIG. 3A, according to one or more examples discussed herein.

For instance, during the progressive scan corresponding to the single image frame 300, the digital image processor unit 106 may further identify a second pair of chords after a pupil center location has been determined based on the first chord 302 and the second chord 304. That is, following the operations discussed above, the digital image processor unit 106 may identify a third chord 330 within a third scanned line 332 and a fourth chord 334 within a fourth scanned line 336. FIG. 3B illustrates one example of the third chord 330 and the fourth chord 334 within the image frame 300 of FIG. 3A. The third chord 330 and fourth chord 334 may be identified by the digital image processor unit 106 in a manner similar to that discussed herein with reference to the first chord 302 and second chord 304. That is, the digital image processor unit 106 may identify the third chord 330 and fourth chord 334 by detecting a start trigger and a stop trigger for each respective chord 330, 334.

As also illustrated in FIG. 3B, the third chord 330 and the fourth chord 334 are separated in the second dimension (e.g., the vertical direction) by a subset of the plurality of lines (indicated by space 342). The subset of the plurality of lines which separates the third chord 330 and the fourth chord 334 may have the same number of lines as the subset of lines that separates the first chord 302 and second chord 304 (e.g., fifteen lines). For purposes of explanation only, the third line 332 has a line number of 370 and the fourth line 336 has a line number of 385. However, in other examples the subset of the plurality of lines that separates the third chord 330 and the fourth chord 334 may have a different number of lines from the subset of lines that separates the first chord 302 and second chord 304.

Once identified, the digital image processor unit 106 may determine a second location of the center of the pupil in the first dimension and in the second dimension based on a two chord crossing of the pupil with the third chord 330 and the fourth chord 334. Similar to FIG. 3A, in FIG. 3B a determined location of the center of the pupil based on the third and fourth chords 330, 334 is illustrated by center indicator 338, and an averaged center location is illustrated by center indicator 340.

The determined location may then be averaged with the center location determined based on the first chord 302 and the second chord 304 to arrive at an average center location. While described herein as performing determinations based on two two-chord pairings (i.e., the first chord 302 and second chord 304, and the third chord 330 and fourth chord 334), in various examples, the digital image processor unit 106 may perform numerous other determinations during the course of a progressive scan of a single image frame. Accordingly, multiple center locations may be determined and averaged to arrive at a highly accurate pupil center location.

While discussed in one example as identifying the third chord 330 and the fourth chord 334 after the first pupil center location has been determined, in other examples, the digital image processor unit 106 may stagger operations performed to identify the start and/or stop triggers of more than one two-chord pairing. For instance, the digital image processor unit 106 may perform operations to identify the start trigger of the third chord 330 while the optical sensor 104 is scanning the requisite number of lines between the first line 314 and the second line 316. Moreover, in certain examples, the digital image processor unit 316 may simultaneously search for more than one two-chord pairing.

As discussed above, in certain examples the number of lines within subset of the plurality of lines between the first line 314 and the second line 316 may be automatically and/or dynamically adjusted by the digital image processor unit 106. As such, in certain examples the digital image processor unit 106 may "re-use" a previously identified chord with a different second chord to generate a second two-chord pairing. For example, once the digital image processing unit 106 has determined a first location of the center of the pupil in the first dimension and in the second dimension based on a two chord crossing of the pupil with the first chord 302 and the second chord 304, the digital image processing unit 106 may identify the third chord 33 and determine a second location of the center of the pupil in the first dimension and in the second dimension based on a two chord crossing of the pupil with the first chord 302 and the third chord 330.

As discussed above, in at least one example the system 100 may include an optical assembly 108, or may be incorporated within an optical device that includes an optical assembly. FIG. 4A illustrates one example of an optical assembly 400, such as the optical assembly 108 shown in FIG. 1. In one example, the optical assembly 400 is a telescope which produces a real exit pupil 414. The optical assembly 400 may include front optics 402, a beamsteering element 404, and an eyepiece 406. Together, the front optics 402 and eyepiece 406 direct and focus incident light onto an operator's eye 408 to allow the operator to view an imaged scene. To effectively view the scene (or entire imaged field of view), the operator must place his/her eye 408 in a plane where the exit pupil 414 of the telescope is formed. At the exit pupil 414, the focused light forms a "bright spot" which may be imaged to reveal the location of the exit pupil 414. Although not illustrated in FIG. 4A, the optical assembly 400 may include a prismatic erector or a lens-based erector, among various other optical elements, for image formation, as known to those skilled in the art.

As shown, the beamsteering element 404 may receive one or more control signals 410 (e.g., from the digital image processor unit 106 of FIG. 1). Control signals may adjust one or more parameters of the beamsteering element 404 to position or re-position the exit pupil 414. In particular, the digital image processor unit may control the beamsteering element 404 to adjustably deflect the beam of light received from the front optics 402 to compensate for movement of the eye 408, and reduce an offset between a determined pupil center location and the real exit pupil 414. As the eye 408 moves away from the optical axis 412 of the assembly 400, the beamsteering element 404 redirects the beam of optical radiation so as to effectively "move" the original eyebox (including the exit pupil) to follow the movement of the eye 408.

Thus, through provision of the larger electronic eyebox, the operator will not experience vignetting or loss of the imaged field of view even when moving the head and/or hands. Control of movement of the eyebox (eyebox delivery) may be accomplished with a closed loop control mode using eye pupil imaging and tracking processes, as discussed herein. That is, the digital image processor unit may compare the determined pupil center location to a position of the exit pupil (e.g., via location of the "bright spot") and provide a control signal 410 to the beamsteering element 404 to reduce the offset between the pupil center location and the "bright spot" and align the exit pupil 414 and the pupil center location.

Figure 4B:
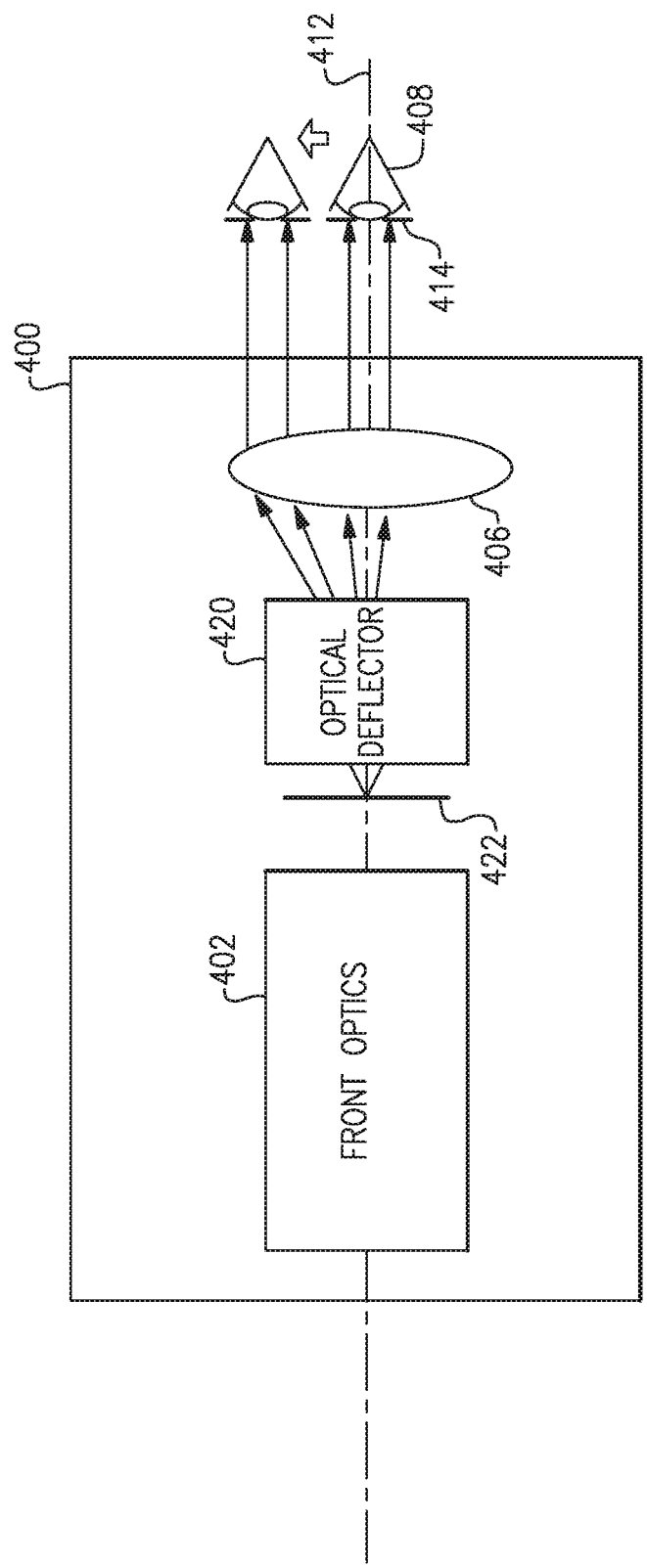
FIG. 4B is a specific example of the optical assembly of FIG. 4A, according to one or more examples discussed herein.

According to one example, the beamsteering element 404 may include an optical deflector. FIG. 4B shows a specific example of the optical assembly 400 of FIG. 4A including an optical deflector 420. As shown, the optical deflector 420 may be located after a final intermediate focal plane 422 of the optical assembly 400. The optical deflector 420 may form part of the eyepiece 406 and/or may be incorporated within the optical assembly 400 or external to the optical assembly 400. In one example, the optical deflector 420 is implemented using field lens. Various examples of controlling an optical deflector to reposition an eyebox are further described in U.S. Pat. No. 9,557,553, issued on Jan. 31, 2017, titled "ELECTRONIC EYEBOX," which is incorporated herein by reference in its entirety.

The digital image processor unit 106 shown and described with reference to FIG. 1 may be implemented using hardware, software, or a combination of hardware and software. For instance, in one example, the digital image processor unit 106 is implemented with a software component that is stored within a data store and executed by a processor. In other examples, the digital image processor unit 106 may include an application-specific integrated circuit (ASIC) that is coupled to a processor. Thus, examples of the digital image processor unit 106 are not limited to a particular hardware or software implementation. One example of a digital image processor unit 500 is illustrated and described with reference to FIG. 5.

As discussed above with reference to FIG. 1, in various examples the high speed pupil detection system 100 includes a digital image processor unit 106 that communicates with at least the optical illuminator 102 and the optical sensor 104. Accordingly, the digital image processor unit 500 of FIG. 5 may include a processor 502, a data store 504, a memory 506, and one or more interfaces, such as a system interface 508 and a user interface 510. While not explicitly illustrated in FIG. 5, in certain examples the digital image processor unit 500 may be coupled to a power source. The power source delivers power to the one or more components of the digital image processor unit 500, as well as, other components of the corresponding pupil detection system.

Figure 5:
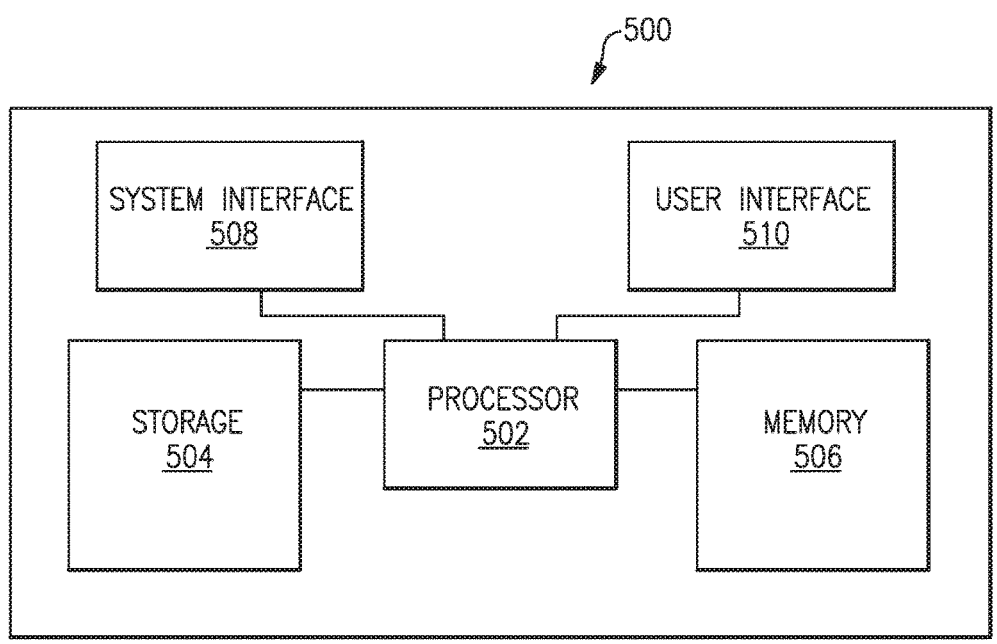
FIG. 5 is a block diagram of a digital image processor unit according to one or more examples discussed herein.

In FIG. 5, the processor 502 is coupled to the data storage 504, memory 508, and the various interfaces. The memory 506 stores programs (e.g., sequences of instructions coded to be executable by the processor 502) and data during operation of the digital image processor unit 500. Thus, the memory 506 may be a relatively high performance, volatile, random access memory such as a dynamic random access memory ("DRAM") or static memory ("SRAM"). However, the memory 506 may include any device for storing data, such as a disk drive or other nonvolatile storage device. Various examples may organize the memory 506 into particularized and, in some cases, unique structures to perform the functions disclosed herein. These data structures may be sized and organized to store values for particular data and types of data.

The data storage 504 includes a computer readable and writeable data storage medium configured to store non-transitory instructions and other data, and can include both nonvolatile storage media, such as optical or magnetic disk, ROM or flash memory, as well as volatile memory, such as RAM. The instructions may include executable programs or other code that can be executed by the at least one processor 502 to perform any of the functions described herein.

In various examples, the digital image processor unit 500 includes several interface components, such as the system interface 508 and the user interface 510 illustrated in FIG. 5. Each of the interface components is configured to exchange, e.g., send or receive, data with other components of the system, or other devices in communication with the digital image processor unit 500. According to various examples, the interface components may include hardware components, software components, or a combination of hardware and software components.

In certain examples, components of the system interface 508 couple the processor 502 to one or more other components of the system 100 shown in FIG. 1, such as the optical illuminator 102 and/or or the optical sensor 104. The system interface 508 may provide one or more control signals to the optical illuminator 102 or optical sensor 104, and may receive one or more responses. Control signals may manage the operation of the optical illuminator 102 and/or optical sensor 104, such as prescribe operation timing and synchronization. In one example, the system interface 508 receives read-out data from the optical sensor 104 (or a ROIC associated with the optical sensor 104), such as the line image data discussed above with reference to at least FIGS. 1, 2, 3A and 3B.

The user interface 510 shown in FIG. 5 may include a combination of hardware and/or software components that allow a corresponding system in which the digital image processor unit 500 is incorporated to communicate with an external entity, such as a user. These components may be configured to receive information from user interactions with the user interface 500. Examples of the components that may be employed within the user interface 510 include buttons, switches, light-emitting diodes, touch screens, displays, stored audio signals, voice recognition, or an application on a computer-enabled device in communication with the digital image processor unit 500. Data received at the various interfaces may be provided to the processor 502, as illustrated in FIG. 5. Communication coupling between the processor 502, memory 506, data storage 504, system interface 508, and user interface 510 may be implemented as one or more physical busses in conformance with specialized or standard computing bus technologies.

The processor 502 performs a series of instructions that result in manipulated data which is stored in and retrieved from the data storage 504, as discussed above. In various examples, the series of instructions result in the calculation of a pupil center location based on one or more two-chord pairs within a received video image frame. Such instructions may correspond to commands for detecting one or more start triggers and/or end triggers, and/or generating one or more two-chord crossings. The processor 502 may be any type of processor, multiprocessor or controller, whether commercially available or specially manufactured. In some examples, the processor 502 may be configured to execute an operating system. The operating system may provide platform services to application software. These platform services may include inter-process and network communication, file system management and standard database manipulation. One or more of many operating systems may be used, and examples are not limited to any particular operating system or operating system characteristic.

Figure 6:
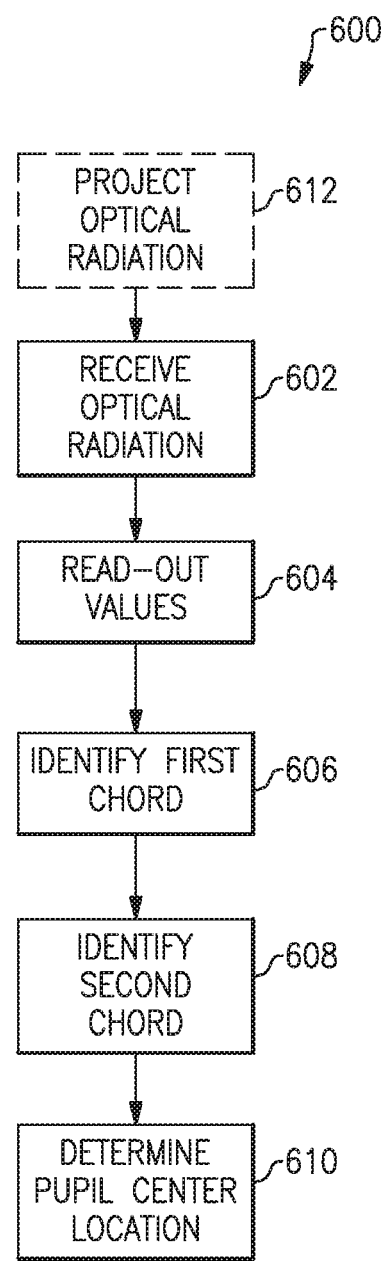
FIG. 6 is a process flow for determining the location of a center of a pupil within a single image frame, according to one or more examples discussed herein.
Figure 7A:
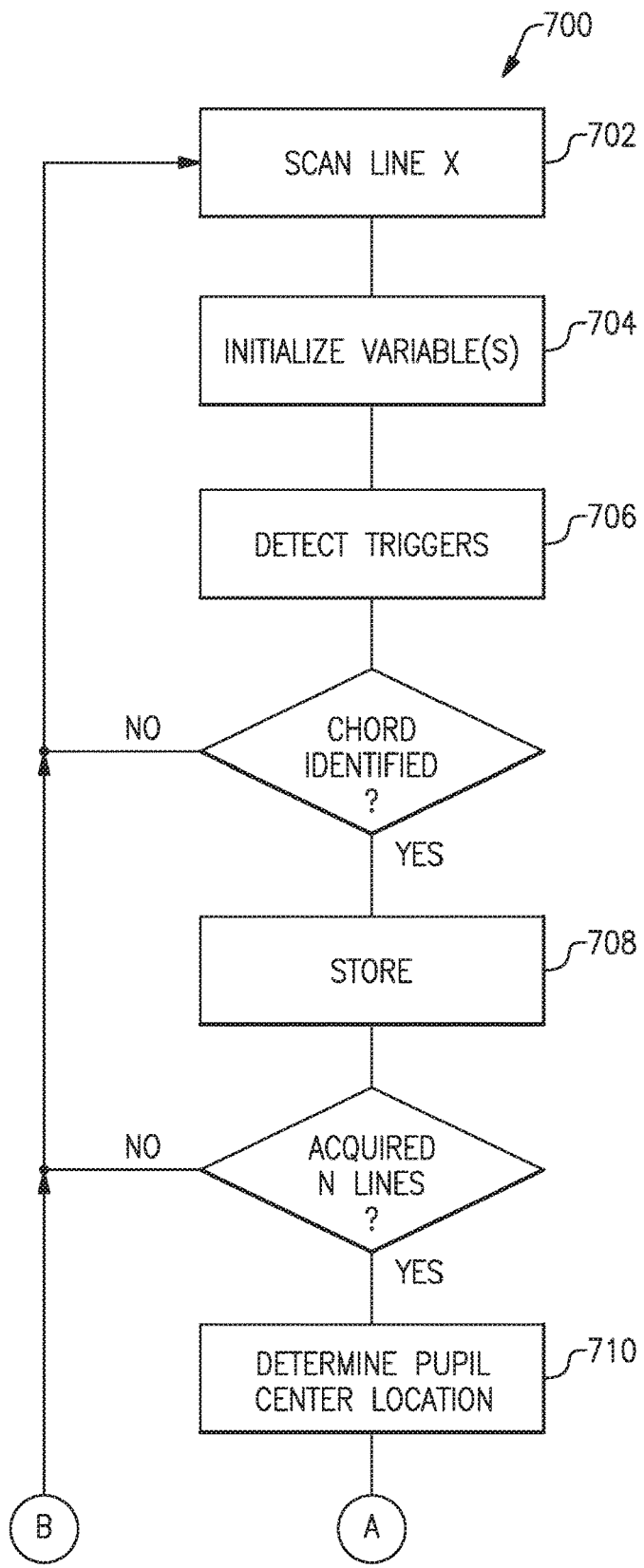
FIG. 7A-7B is a more detailed process flow for determining the location of a center of a pupil within a single image frame, according to one or more examples discussed herein.

As described above with reference to at least FIGS. 1, 2A, and 2B, several examples perform processes for determining the location of a center of a pupil from a single image frame of a continuous video image stream. In some examples, these processes are executed by a high speed pupil detection system, such as the system 100 described above with reference to FIGS. 1, 2A, and 2B. One example of such a process 600 is illustrated in FIG. 6. Process 600 includes the acts of receiving optical radiation at one or more pixels of an optical sensor, reading-out a value of the one or more pixels in a plurality of lines, identifying a first chord, identifying a second chord, and determining a pupil center location. As illustrated, the process 600 may also include the act of projecting optical radiation onto an eye. The process 600 of FIG. 6 is described with continuing reference to the high speed pupil detection system 100 of FIG. 1 and the corresponding optical sensor 104 illustrated in FIG. 2.

In act 602, the process 600 includes receiving optical radiation reflected from an eye at one or more pixels of an optical sensor. As discussed above with reference to FIG. 2, the optical sensor includes a plurality of individual detector elements, which may be referred to as pixels. In act 602, each pixel of the plurality collects and integrates photons of the received optical radiation to provide a read-out value representative of the accumulated flux of the incident optical radiation. In certain examples, the process 600 may include projecting optical radiation onto the eye with an optical illuminator (e.g., act 612). Accordingly, in certain examples, act 602 includes receiving reflections from the eye of the optical radiation projected by the optical illuminator. As discussed above, the optical radiation may include infrared radiation, such as infrared radiation within the short-wavelength infrared (SWIR) wavelength band.

In act 604, the process 600 may include reading-out the value of the one or more pixels in a plurality of lines to progressively generate a first image frame of a video image stream, the value of the one or more pixels being based on the flux of the received optical radiation. In one example, act 604 includes progressively scanning (i.e., reading-out) the values of the pixels line by line to build up a full image frame of the eye. That is, in one example lines of pixels within the optical sensor are scanned (e.g., by a ROIC) in a sequential, line-by-line manner. Although the term "line" may generally be used to refer to a set of pixels in a horizontal direction, it may equally refer to a set of pixels in the vertical direction.

In act 606, based on the scanned read-out values, the process 600 may include identifying a first chord within a first line of the plurality of progressively scanned lines. As discussed above with reference to FIGS. 1, 2, 3A, and 3B, in at least one example, a chord is a portion of a scanned line which extends between a start trigger and a stop trigger. Accordingly, identifying the first chord may include detecting a first start trigger and detecting a first stop trigger. In act 608, the process 600 includes identifying a second chord within a second line of the plurality of scanned lines, the second chord being separated from the first chord by a subset of the plurality of scanned lines. Similar to the first chord, the second chord may be identified by detecting a second start trigger and detecting a second stop trigger. The start trigger indicates the beginning of the corresponding chord and the stop trigger indicates the end of the corresponding chord.

In act 610, the process 600 includes determining a location of the center of a pupil of the eye in a first dimension and in a second dimension based on a two chord crossing of the pupil with the first chord and the second chord. In at least one example, act 608 includes determining the location of the center of the pupil by determining a location of the center of the pupil in the first dimension, determining an intermediary center, and determining the location of the center of the pupil in the second dimension.

While not explicitly illustrated in FIG. 6, the process 600 may include various other acts and sub-processes. FIG. 7 illustrates a more detailed process flow of the process 600 shown in FIG. 6. That is, FIG. 7 illustrates one example of a more detailed process flow for determining the location of a center of a pupil from a single image frame of a continuous video image stream.

In act 702, the process 700 may include scanning the value of the one or more pixels in a first line across the optical sensor. Further details of the scan are described above with reference to act 604 of FIG. 6. In act 704, the process 700 may include the act of initializing (e.g., assigning) a line iteration number of the first scanned line. Each line iteration number may be relative to a direction in which the optical radiation is scanned. For instance, scans in a first dimension (e.g., horizontal direction) may be incremented as X1, X2, X3, X4, and etc., and scans in a second dimension orthogonal to the first dimension (e.g., vertical direction) may be incremented as Y1, Y2, Y3, Y4, and etc. Each subsequent scan may increase the line iteration number by one increment.

Once the line iteration number for the given line has been scanned, the process 700 may include the act of searching the line image data of the scanned line for a first chord (act 706). As shown in FIG. 6, act 706 may include searching for and detecting a start trigger and a stop trigger for the first chord. As discussed above with reference to at least FIG. 3A, processes for detecting a start trigger and/or a stop trigger may include the acts of analyzing the line image data corresponding to a scanned line and detecting a transition in a brightness level along the line image data.

If a first chord is not detected, the process 700 returns to acts 702 and 704 where a subsequent line is scanned, and the line number is increased by one increment. However, if the first chord is detected, the process 700 proceeds to act 708. In act 708, the process may include storing the coordinates of the detected first chord (e.g., at the data storage 504 illustrated in FIG. 5). In one example, act 708 may include storing the line number, a coordinate in the first dimension of the start trigger and the stop trigger of the first chord, and a coordinate in the second dimension of the start trigger and stop trigger of the first chord.

Once the information descriptive of the first chord is stored, the process 700 may include determining whether the subset of the plurality of scanned lines has been met. That is, the process 700 may include comparing a difference between a current line iteration number and the line iteration number of the first chord to the value of the subset of the plurality of lines. If the value of the subset of the plurality of lines is met, the process 700 may then include searching the line image data of the current scanned line for a second chord. That is, once the difference between the line iteration number of a current scanned line and the line iteration number of the first chord has met the threshold specified by the subset of the plurality of lines, the process 700 may include detecting a start trigger and/or a stop trigger of the second chord. However, if the value of the subset of the plurality of lines is not met, the process 700 returns to acts 702 and 704 where a subsequent line is scanned, and the line number is increased by one increment.

In act 710, the process 700 includes determining a location of the center of a pupil of the eye in the first dimension and the second dimension based on a two chord crossing of the pupil with the first chord and the second chord. Acts for determining the location of the pupil center are discussed above with reference to act 610 of FIG. 6.

In acts 712 and 714, the process 700 may include incrementing a variable (e.g., counter) assigned to the determined pupil center and storing the pupil center location. In particular, each pupil center location may be stored as a series of coordinates relative to the image frame. As discussed above with reference to FIG. 1, in many instances optical radiation reflected from the imaged eye is received at an optical sensor which includes a plurality of pixels arranged in a series of rows and columns. Accordingly, in acts 712 and 714, the process 700 may include assigning the pupil center location a first coordinate that corresponds to a pixel location in the first dimension (e.g., horizontal direction), and a second coordinate that corresponds to a pixel location in the second dimension (e.g., vertical direction). In act 714, the coordinates may be stored along with the corresponding counter.

Figure 7B:
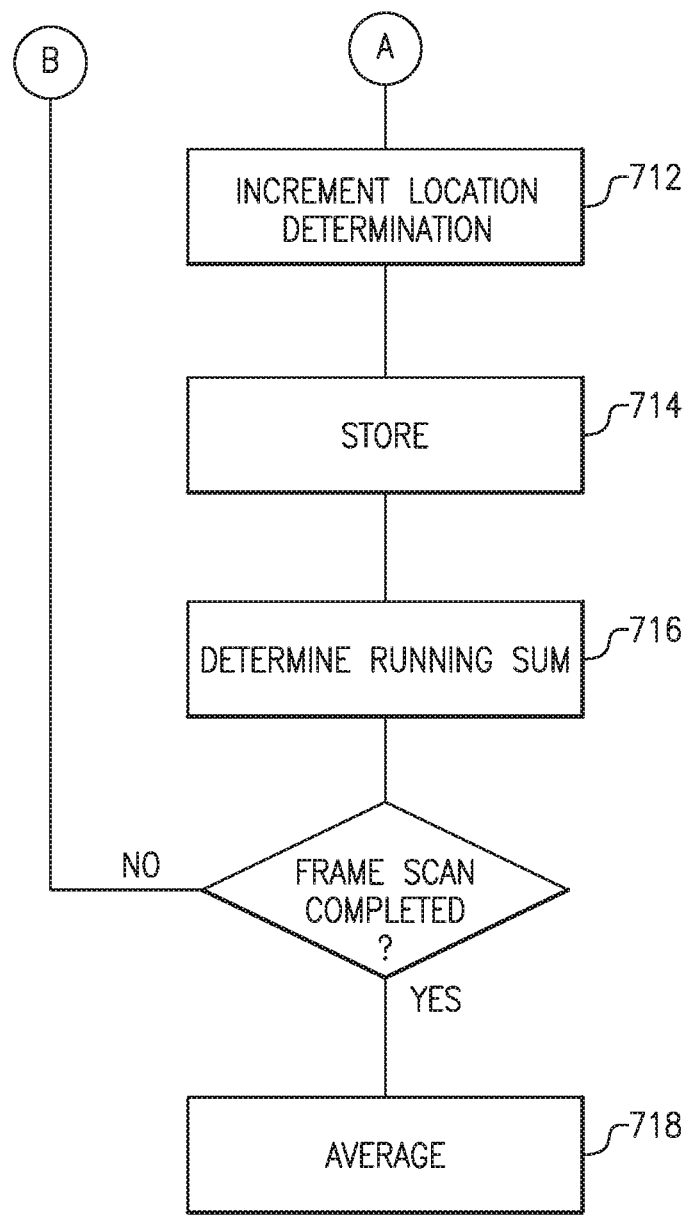

As illustrated in FIG. 7B, in many instances the process 700 may include performing multiple pupil center location determinations for a single image frame. At the completion of each determination, the process 700 may include determining a running sum of the calculated coordinates. For instance, the process 700 may include summing the first coordinates of each center location, and summing the second coordinates of each center location (act 716). This process may repeat until a full scan of the eye (i.e., a full image frame) is complete. In act 718, the process 700 may include averaging the coordinates of the determined pupil center locations to determine an average pupil center location.

Accordingly, aspects and embodiments are generally directed to a high speed pupil detection system and method that reduce the computational complexity of current pupil tracking techniques. In some examples, pupil positioning measurements performed during a single image frame of a continuous video stream substantially increases the speed by which corrective measures may be performed by an associated optical device. Accordingly, various aspects and embodiments of the pupil detection system and method described herein provide high speed and real time pupil detection functionality which is not currently offered by existing optical devices and imaging techniques.

Having described above several aspects of at least one example, it is to be appreciated various alterations, modifications, and improvements will readily occur to those skilled in the art. Such alterations, modifications, and improvements are intended to be part of this disclosure and are intended to be within the scope of the invention. Accordingly, the foregoing description and drawings are by way of example only, and the scope of the invention should be determined from proper construction of the appended claims, and their equivalents.

What is claimed is:

1. A method of pupil detection, the method comprising:
receiving optical radiation reflected from an eye at one or more pixels of an optical sensor;
reading-out a value of each of the one or more pixels in a plurality of lines to progressively generate a first image frame of a video image stream, the value of each of the one or more pixels being based on a flux of the received optical radiation;
identifying a first chord within a first line of the plurality of lines by detecting a first start trigger and detecting a first stop trigger, the first chord being between the first start trigger and the first stop trigger;
identifying a second chord within a second line of the plurality of lines by detecting a second start trigger and detecting a second stop trigger, the second chord being between the second start trigger and the second stop trigger and separated from the first chord by a subset of the plurality of lines; and
determining a first location of a center of a pupil of the eye in a first dimension and in a second dimension orthogonal to the first dimension based on a crossing of the pupil by both the first chord and the second chord, wherein determining the first location of the center of the pupil in the first dimension includes determining the first location of the center of the pupil in the first dimension according to:

$$C_X = \frac{Stop_1 - Start_1}{2} + Start_1$$

wherein $C_X$ is the location of the center of the pupil in the first dimension, $Stop_1$ is a coordinate of the first stop trigger, and $Start_1$ is a coordinate of the first start trigger, and wherein determining the first location of the center of the pupil in the second dimension includes determining an intermediary center according to:

$$Center = \frac{\left(\frac{Stop_2 - Start_2}{2}\right)^2 - \left(\frac{Stop_1 - Start_1}{2}\right)^2 - ChordSpacing^2}{2 * ChordSpacing}$$

wherein Center is the intermediary center, $Stop_2$ is a coordinate of the second stop trigger, $Start_2$ is a coordinate of the second start trigger, and ChordSpacing is the subset of the plurality of lines.

2. The method of claim 1, wherein identifying the first chord includes identifying the first chord while reading-out the value of each of the one or more pixels, and wherein identifying the second chord includes identifying the second chord while reading-out the value of each of the one or more pixels.

3. The method of claim 2, further comprising:
identifying a third chord within a third line of the plurality of lines, while reading-out the value of each of the one or more pixels;
identifying a fourth chord within a fourth line of the plurality of lines, while reading-out the value of each of the one or more pixels; and
determining a second location of the center of the pupil in the first dimension and in the second dimension based on a crossing of the pupil by both the third chord and the fourth chord.

4. The method of claim 3, further comprising averaging the first location and the second location.

5. The method of claim 1, wherein each of the first start trigger and the first stop trigger include a transition in a brightness level along the first line, and wherein each of the second start trigger and the second stop trigger include a transition in a brightness level along the second line.

6. The method of claim 5, wherein the transition in the brightness level along the first line is an intersection point between the first line and a perimeter of the pupil, and wherein the transition in the brightness level along the second line is an intersection point between the second line and the perimeter of the pupil.

7. The method of claim 1, wherein determining the location of the center of the pupil of the eye in the second dimension includes determining the location of the center of the pupil in the second dimension according to:

$$C_Y = \text{LineNumber} + \text{ChordSpacing} + \text{Center}$$

wherein $C_Y$ is the location of the center of the eye in the second dimension and LineNumber is a line iteration number of the second line of the plurality of lines.

8. The method of claim 1, further comprising projecting optical radiation onto the eye with an infrared illuminator, the optical radiation including infrared radiation.

9. The method of claim 1, further comprising adjusting a beamsteering element of an optical assembly to position a real exit pupil to reduce an offset between the first location of the center of the pupil and the real exit pupil.

10. A pupil detection system comprising:
an optical illuminator configured to project optical radiation onto an eye;
an optical sensor positioned to receive reflections of the optical radiation from the eye and progressively generate in a plurality of lines a first image frame of a video image stream; and
a digital image processor unit coupled to at least the optical sensor and configured to:
identify a first chord within a first line of the plurality of lines by detecting a first start trigger and detecting a first stop trigger, the first chord being between the first start trigger and the first stop trigger;
identify a second chord within a second line of the plurality of lines, by detecting a second start trigger and detecting a second stop trigger, the second chord being between the second start trigger and the second stop trigger and separated from the first chord by a subset of the plurality of lines; and
determine a first location of a center of a pupil of the eye in a first dimension and in a second dimension orthogonal to the first dimension based on a crossing of the pupil by both the first chord and the second chord, including determining the first location of the center of the pupil in the first dimension according to:

$$C_X = \frac{Stop_1 - Start_1}{2} + Start_1$$

wherein $C_X$ is the location of the center of the pupil in the first dimension, $Stop_1$ is a coordinate of the first stop trigger, and $Start_1$ is a coordinate of the first start trigger, and determining the first location of the center of the pupil in the second dimension by determining an intermediary center according to:

$$Center = \frac{\left(\frac{Stop_2 - Start_2}{2}\right)^2 - \left(\frac{Stop_1 - Start_1}{2}\right)^2 - ChordSpacing^2}{2 * ChordSpacing}$$

wherein Center is the intermediary center, $Stop_2$ is a coordinate of the second stop trigger, $Start_2$ is a coordinate of the second start trigger, and ChordSpacing is the subset of the plurality of lines.

11. The pupil detection system of claim 10, wherein the optical illuminator is an infrared illuminator positioned to project infrared radiation onto the eye.

12. The pupil detection system of claim 10, further comprising an optical assembly including at least an eyepiece configured to produce a real exit pupil, wherein the digital image processor is further configured to adjust the optical assembly to position the real exit pupil to reduce an offset between the first location of the center of the pupil and the real exit pupil.

13. The pupil detection system of claim 10, wherein the digital image processor is further configured to identify the first chord while the optical sensor progressively generates the first image frame, and identify the second chord while the optical sensor progressively generates the first image frame.

14. The pupil detection system of claim 13, wherein the digital image processor is further configured to:
- identify a third chord within a third line of the plurality of lines, while the optical sensor progressively generates the first image frame;
- identify a fourth chord within a fourth line of the plurality of lines, while the optical sensor progressively generates the first image frame;
- determine a second location of the center of the pupil in the first dimension and in the second dimension based on a crossing of the pupil by both the third chord and the fourth chord; and
- average the first location and the second location.

15. The pupil detection system of claim 10, wherein each of the first start trigger and the first stop trigger include a transition in a brightness level along the first line, and wherein each of the second start trigger and the second stop trigger include a transition in a brightness level along the second line.

* * * * *